US012757896B2

(12) United States Patent
Hänsel et al.

(10) Patent No.: US 12,757,896 B2
(45) Date of Patent: Oct. 13, 2026

(54) USE OF POLYGLYCEROL ESTERS AS CARRIERS FOR MICROBIOLOGICAL ACTIVE INGREDIENTS

(71) Applicant: Evonik Operations GmbH, Essen (DE)

(72) Inventors: René Hänsel, Dorsten (DE); Alissa Singer, Weiterstadt (DE); Katja Skrabania, Essen (DE); Jochen Kleinen, Heinsberg (DE); Tanja Berger, Essen (DE); Kevin Kleinschmidt, Gelsenkirchen (DE)

(73) Assignee: Evonik Operations GmbH, Essen (DE)

( * ) Notice: Subject to any disclaimer, the term of this patent is extended or adjusted under 35 U.S.C. 154(b) by 1070 days.

(21) Appl. No.: 17/612,105

(22) PCT Filed: May 12, 2020

(86) PCT No.: PCT/EP2020/063123

§ 371 (c)(1),
(2) Date: Nov. 17, 2021

(87) PCT Pub. No.: WO2020/234035

PCT Pub. Date: Nov. 26, 2020

(65) Prior Publication Data

US 2022/0211036 A1 Jul. 7, 2022

(30) Foreign Application Priority Data

May 20, 2019 (EP) ..................................... 19175286

(51) Int. Cl.

| | |
|---|---|
| ***A01N 25/30*** | (2006.01) |
| ***A01N 63/20*** | (2020.01) |
| ***A01N 63/22*** | (2020.01) |
| ***A23K 10/18*** | (2016.01) |
| ***A23L 29/10*** | (2016.01) |
| ***A23L 33/135*** | (2016.01) |
| ***A61K 35/741*** | (2015.01) |

(52) U.S. Cl.
CPC ............. *A01N 25/30* (2013.01); *A01N 63/20* (2020.01); *A01N 63/22* (2020.01); *A23K 10/18* (2016.05); *A23L 29/10* (2016.08); *A23L 33/135* (2016.08); *A61K 35/741* (2013.01)

(58) Field of Classification Search
CPC ................................ A23K 10/10; A01N 25/30
See application file for complete search history.

(56) References Cited

U.S. PATENT DOCUMENTS 3,793,465 A * 2/1974 Bohren ................ A23C 9/1232 426/585
3,839,571 A 10/1974 Ciccone et al.
4,000,258 A 12/1976 Shieh et al.
5,247,114 A 9/1993 Jakobson et al.
5,424,469 A 6/1995 Jakobson et al.
5,466,719 A 11/1995 Jakobson et al.
6,242,499 B1 6/2001 Gruning et al.
7,906,664 B2 3/2011 Allef et al.
8,227,399 B2 7/2012 Wenk et al.
8,598,083 B2 * 12/2013 Kaminskyj ............. C05F 11/08 435/945
8,664,175 B2 3/2014 Wenk et al.
8,703,159 B2 4/2014 Wenk et al.
8,993,792 B2 3/2015 Hartung et al.
9,409,853 B2 8/2016 Schuch et al.
9,427,385 B2 8/2016 Meyer et al.
9,738,797 B2 8/2017 Nilewski et al.
9,776,951 B2 10/2017 Friedrich et al.
9,788,551 B2 10/2017 Lüth
10,292,925 B2 5/2019 Gu et al.
10,299,471 B2 5/2019 Hänsel et al.
10,390,530 B2 * 8/2019 Klostermann ......... A01N 25/04
11,234,441 B2 2/2022 Hänsel et al.
2003/0008917 A1 1/2003 Brock et al.
2003/0065027 A1 4/2003 Brock et al.
2005/0170053 A1 * 8/2005 Milani ...................... B65B 9/12 426/414
2006/0165627 A1 7/2006 Allef et al.

(Continued)

FOREIGN PATENT DOCUMENTS

CN 106417620 A * 2/2017 ............ A23C 11/06
DE 10 2012 010 012 A1 11/2012

(Continued)

OTHER PUBLICATIONS

XP55611940, "*Break-Thru SP 133 Product Label*", Hopewell, VA, U.S.A., May 9, 2017, pp. 1-2.

(Continued)

*Primary Examiner* — Gina C Justice
(74) *Attorney, Agent, or Firm* — Grüneberg Global IP, PLLC

(57) ABSTRACT

Compositions containing at least one polyglycerol ester and preferably, at least one emulsifier, can be used as a carrier for an active microbiological ingredient. Compositions containing both the carrier and the active microbiological ingredient are useful; and methods of increasing the storage stability of the active microbiological ingredient can be used with the composition. These compositions can be also used for the treatment of plants, for the treatment of seed, for the treatment of soils, as a biostimulant, as a probiotic food supplement, or as a probiotic animal feed additive.

18 Claims, No Drawings

(56) References Cited

U.S. PATENT DOCUMENTS

| | | | | |
|---|---|---|---|---|
| 2007/0191229 | A1 | 8/2007 | Pompeo et al. | |
| 2011/0014255 | A1* | 1/2011 | Balastre | A01N 25/02 977/773 |
| 2011/0028424 | A1 | 2/2011 | Zhang et al. | |
| 2011/0201533 | A1 | 8/2011 | Ponder et al. | |
| 2011/0201534 | A1 | 8/2011 | Ponder et al. | |
| 2011/0201538 | A1 | 8/2011 | Wenk et al. | |
| 2012/0308503 | A1 | 12/2012 | Wenk et al. | |
| 2012/0309667 | A1 | 12/2012 | Wenk et al. | |
| 2012/0309996 | A1 | 12/2012 | Wenk et al. | |
| 2013/0204021 | A1 | 8/2013 | Hartung et al. | |
| 2013/0281552 | A1 | 10/2013 | Nilewski et al. | |
| 2014/0072521 | A1 | 3/2014 | Meyer et al. | |
| 2014/0212387 | A1 | 7/2014 | Lüth | |
| 2015/0315123 | A1 | 11/2015 | Schuch et al. | |
| 2016/0340290 | A1 | 11/2016 | Friedrich et al. | |
| 2017/0202770 | A1 | 7/2017 | Friedrich et al. | |
| 2017/0295782 | A1 | 10/2017 | Klostermann et al. | |
| 2018/0036218 | A1 | 2/2018 | Gu et al. | |
| 2018/0042235 | A1 | 2/2018 | Colon et al. | |
| 2018/0125067 | A1 | 5/2018 | Hänsel et al. | |
| 2019/0037838 | A1 | 2/2019 | Klostermann et al. | |
| 2019/0059385 | A1 | 2/2019 | Hänsel et al. | |
| 2021/0145010 | A1 | 5/2021 | Hänsel et al. | |
| 2021/0315952 | A1 | 10/2021 | Farmer et al. | |
| 2022/0315799 | A1 | 10/2022 | Hänsel et al. | |
| 2023/0200380 | A1 | 6/2023 | Hänsel et al. | |

FOREIGN PATENT DOCUMENTS

| | | | |
|---|---|---|---|
| EP | 0299295 | | 1/1989 |
| EP | 0636317 | | 2/1995 |
| EP | 2243462 | | 10/2010 |
| GB | 1 593 354 | A | 7/1981 |
| WO | 93/24013 | A2 | 12/1993 |
| WO | 02/069705 | A1 | 9/2002 |
| WO | 2011026983 | | 3/2011 |
| WO | 2012/163322 | | 12/2012 |
| WO | 2014/122196 | A1 | 8/2014 |
| WO | 2015069708 | | 5/2015 |
| WO | 2016/050726 | | 4/2016 |
| WO | 2016/055344 | | 4/2016 |
| WO | 2017/116837 | A1 | 7/2017 |
| WO | 2017210512 | | 12/2017 |
| WO | 2018/078067 | | 5/2018 |
| WO | 2019/011825 | A1 | 1/2019 |
| WO | 2019/162360 | A1 | 8/2019 |
| WO | 2019/201777 | A1 | 10/2019 |
| WO | 2020/011819 | A1 | 1/2020 |
| WO | 2021/083989 | A1 | 5/2021 |

OTHER PUBLICATIONS

XP55611941,"*Spray Adjuvants Registered for Use Aquatic Sites in Washington*", Washington State Department of Agriculture, Pesticide Management Division, Registration and Licensing Service Program, Olympia, WA, U.S.A., May 15, 2017, pp. 1-5.

U.S. Appl. No. 07/209,630, filed Jun. 21, 1988, Volkbert Bade.

U.S. Appl. No. 08/281,052, filed Jul. 27, 1994, Haehnel et al.

U.S. Appl. No. 10/126,738, filed Apr. 18, 2002, 2003/0008917, Brock et al.

U.S. Appl. No. 10/126,186, filed Apr. 18, 2002, 2003/0065027, Brock et al.

U.S. Pat. No. 7,906,664, Mar. 15, 2011, 2006/0165627, Allef et al.

U.S. Appl. No. 12/844,011, filed Jul. 27, 2010, 2011/0028424, Zhang et al.

U.S. Pat. No. 8,664,175, Mar. 4, 2014, 2012/0309667, Wenk et al.

U.S. Pat. No. 8,227,399, Jul. 24, 2012, 2011/0201538, Wenk et al.

U.S. Pat. No. 8,703,159, Apr. 22, 2014, 2012/0309996, Wenk et al.

U.S. Appl. No. 13/578,130, filed Aug. 9, 2012, Wenk et al.

U.S. Appl. No. 61/303,849, filed Feb. 12, 2010, Ponder et al.

U.S. Appl. No. 13/024,385, filed Feb. 10, 2011, Ponder et al.

U.S. Appl. No. 61/303,873, filed Feb. 12, 2010, Ponder et al.

U.S. Appl. No. 13/024,413, filed Feb. 10, 2011, Ponder et al.

U.S. Appl. No. 61/594,620, filed Feb. 3, 2012, Hartung et al.

U.S. Pat. No. 8,993,792, Mar. 31, 2015, 2013/0204021, Hartung et al.

U.S. Pat. No. 9,738,797, Aug. 22, 2017, 2013/0281552, Nilewski et al.

U.S. Pat. No. 9,427,385, Aug. 30, 2016, 2014/0072521, Meyer et al.

U.S. Pat. No. 9,409,853, Aug. 9, 2016, 2015/0315123, Schuch et al.

U.S. Pat. No. 10,292,925, May 21, 2019, 2018/0036218, Gu et al.

U.S. Pat. No. 9,776,951, Oct. 3, 2017, 2016/0340290, Friedrich et al.

U.S. Pat. No. 10,390,530, Aug. 27, 2019, 2017/0295782, Klostermann et al.

U.S. Appl. No. 15/380,137, filed Dec. 15, 2016, Friedrich et al.

"Dowicide G-ST Antimicrobial", Antimicrobial Agents, Section I-11 revised, The DOW Chemical Company, https://www3.epa.gov/pesticides/chem_search/ppls/001022-00527-19761004.pdf, Oct. 4, 1976, 8 pages.

European Extended Search Report dated Sep. 16, 2020, in European Patent Application No. 20172266.7, 12 pages.

Office Action received for U.S. Appl. No. 17/997,202, mailed on May 12, 2025, 16 pages.

International Search Report dated Jun. 17, 2021, in PCT/EP2021/060659, 10 pages with English translation.

"Polyalkylene Glycol Monobutyl Ether (PGME)—Handling/Processing", Technical Evaluation Report, Compiled by the USDA AMS Agricultural Analytics Division for the USDA National Organic Program, Jun. 7, 2013, pp. 1-17.

"UCON 50-HB-660 PPG 12-BUTETH-16 Copolymer 55 Gallon Drum", Jan. 1, 2020, 1 page.

Written Opinion dated Jun. 17, 2021, in PCT/EP2021/060659, 13 pages with English translation.

European Search Report issued Aug. 21, 2019 in European Application No. 19175286.4, 10 pages.

International Search Report issued Aug. 5, 2020 in PCT/EP2020/063123, 7 pages with English translation.

Written Opinion issued Aug. 5, 2020 in PCT/EP2020/063123, 11 pages with English translation.

* cited by examiner

USE OF POLYGLYCEROL ESTERS AS CARRIERS FOR MICROBIOLOGICAL ACTIVE INGREDIENTS

CROSS-REFERENCE TO RELATED APPLICATIONS

This application is the National Stage entry under § 371 of International Application No. PCT/EP2020/063123, filed on May 12, 2020, and which claims the benefit of priority to European Application No. 19175286.4, filed on May 20, 2019. The content of each of these applications is hereby incorporated by reference in its entirety.

BACKGROUND OF THE INVENTION

Field of the Invention

The present invention relates to the use of compositions comprising at least one polyglycerol ester and preferably at least one emulsifier as carrier for at least one active microbiological ingredient; to compositions comprising both the carrier and the active microbiological ingredient; to methods of increasing the storage stability of the active microbiological ingredient; and to the use of these compositions for the treatment of plants, for the treatment of seed, for the treatment of sols, as biostimulant, as probiotic food supplement or probiotic animal feed additive.

Description of Related Art

In agriculture, microorganisms are used for a multitude of beneficial applications, for example for biological plant protection, for biological plant fortification or for biological soil improvement. In addition, compositions comprising living microorganisms are also used for the treatment of seed. The field of use is thus especially agriculture and forestry including horticulture and pomiculture, and the growing of ornamentals and the growing and care of lawns. In addition, compositions comprising living microorganisms are also employed as probiotics in foods and animal feeds or as probiotic medicaments.

Biological plant protection products—also referred to as biopesticides—are increasingly being used in agriculture since they help to replace or reduce the use of chemical pesticides, and thus reduce residues of chemical pesticides in foods. In the event of resistances of plant pathogens and pests to chemical pesticides, biological plant protection products are alternatives. The use of biological plant protection products is increasingly being promoted by current environmental legislation, since they make use of natural regulation mechanisms that have evolved over the course of evolution, and hence conserve the environment. Biological plant protection products find use, for example, as fungicides, insecticides, nematicides or herbicides and are being used for preventative treatment or curative control of plant pathogens and pests. Active biological ingredients are specified, for example, in *The Manual of Biocontrol Agents,* 2001, The British Crop Protection Council.

According to Article 2 (1) of REGULATION (EC) No 1107/2009 OF THE EUROPEAN PARLIAMENT AND OF THE COUNCIL of 21 Oct. 2009 concerning the placing of plant protection products on the market and repealing Council Directives 79/117/EEC and 91/414/EEC, plant protection products refer to products, in the form in which they are supplied to the user, consisting of or containing active substances, safeners or synergists, and intended for one of the following uses:

a) protecting plants or plant products against all harmful organisms or preventing the action of such organisms, unless the main purpose of these products is considered to be for reasons of hygiene rather than for the protection of plants or plant products;
b) influencing the life processes of plants, such as substances influencing their growth, other than as a nutrient;
c) preserving plant products, in so far as such substances or products are not subject to special Community provisions on preservatives;
d) destroying undesired plants or parts of plants, except algae unless the products are applied on soil or water to protect plants;
e) checking or preventing undesired growth of plants, except algae unless the products are applied on soil or water to protect plants.

The present invention is preferably based on the above-mentioned definition of the term “plant protection products”.

According to the provisional definition of the European Biostimulants Industry Council (EBIC), biostimulants contain substance(s) and/or microorganisms whose function when applied to plants or the rhizosphere is to stimulate natural processes to enhance/benefit nutrient uptake, nutrient efficiency, tolerance to abiotic stress, and crop quality (http://www.biostimulants.eu/). For example, the microorganisms *Trichoderma* spp., *Pythium oligandrum, Bacillus* spp., *Pseudomonas* spp. and *Streptomyces* spp. can cause reactions in plants that lead to elevated resistance to pathogens or other stress factors, such as drought, poor nutrient supply, unfavourable pH values and/or high salt content in the soil. The microorganisms *Trichoderma* spp., *Penicillium bilaii, Azotobacter* spp., *Azotomonas* spp., *Azospirillum* spp. and *Rhizobium* spp. can lead, for example, to an improvement in nutrient availability in the soil or directly at the plant roots.

Barriers to broad use of active microbiological ingredients for biological plant protection, for biological plant fortification or for biological soil improvement have to date been their lower efficacy compared to many chemical products. This lower efficacy is based, for example, on inadequate survival capacity of the microorganisms in the formulation during storage. In application, possibly too little active ingredient reaches the target locus on the plant or in the soil, where it may be rapidly degraded by environmental effects. However, these disadvantageous aspects can be improved by a suitable carrier.

The biological plant protection product based on microorganisms as active constituent and the biostimulants are typically diluted in water in the form of a formulation prior to use. These formulations may, for example, be sold formulations, such as wettable powders (WP) or water-dispersible granules (WG), but also liquid formulations such as oil dispersions (OD), suspension concentrates (SC) or dispersion concentrates (DC).

The carrier brings the microorganisms into a form in which they can be handled, such that they can be distributed and applied in water. Since many microorganisms such as some genera of fungal conidia are water-repellent, a particular task of the carrier is to make them water-compatible. Moreover, the formulation should also assure the survival capacity of the microorganisms during transport and storage. The carrier is also to ensure that employment is possible by means of spraying equipment. The aggregation of the microorganisms is thus to be prevented, in order that blockage of nozzles can be ruled out. The carrier is advantageously also to contain those substances that assure the dispersion and distribution of microorganisms in the water, and facilitate the application of the spray liquor to the plants or the soil.

In practice, formulations of chemical and biological plant protection products are diluted in water by the user prior to use. For this purpose, the plant protection products are typically added to a tank with water as ingredient and distributed in what is called the spray liquor while stirring. This spray liquor is a ready-to-use dilution of the plant protection products. For cultivation of agricultural areas, these spray liquors are atomized over the plants to be treated. In this connection, atomization means the droplet formation as a result of mechanical action on a liquid medium, preferably by rotation of objects and/or as a result of decompression (reduction in pressure) at small openings. The spray liquor is more preferably applied in the form of a spray generated with the aid of nozzles. For the cultivation of agricultural areas, generally 100 to 1000 litres, optimally 100 to 400 litres, of spray liquor are sprayed per hectare. In exceptional cases, however, departure from these limits is possible. The limits may thus quite possibly vary upward or downward. For example, in what are called low-volume applications, very small volumes down to 1.5 l/ha are sprayed, whereas in the case of application by what is called lance technology very high volumes up to 15 000 l/ha can be achieved. The atomization process here can take place either from high altitudes, for example by means of the spraying of spray liquors from an aeroplane, or from altitudes close to the earth, for example by spraying spray liquors by means of a tractor-mounted sprayer. Other equipment, such as spraying lances, or back-spraying are likewise known for applying spray liquors. The spray liquor is thus typically sprayed by means of a nozzle onto the plants or the soil in a defined dosage. The spray droplets are to be well distributed on the plant or the soil in order that an optimal effect is assured.

For improvement of the biological efficacy (also referred to as effectiveness) of chemical plant protection products, it is standard practice to use what are called adjuvants, also referred to as additives. Adjuvants are typically added to the aqueous spray liquor shortly before deployment and spray application as tankmix additive or integrated directly into plant protection product formulations. The adjuvants are typically added to the spray liquor in concentrations of 0.001% by volume to 1% by volume. The adjuvants reduce the surface tension of water and ensure improved adhesion and wetting of the spray droplets on the hydrophobic leaves of the plant, and hence homogeneous distribution of the plant protection product over a wide area. They also improve the penetration and distribution of the active constituents of the spray liquor into the sol. This increases biological efficacy. Adjuvants can likewise also improve the efficacy of microbiological plant protection products and, depending on the nature of the formulation, be used as dispersant, emulsifier and wetting agent. However, they may potentially be cytotoxic to living microorganisms and have to date only been used rarely for formulations of living microorganisms. It is particularly advantageous when the adjuvant is not mixed with the active biological ingredient only on production of the spray liquor, but is suitable as a carrier for the active biological ingredient.

The Pesticides Safety Directorate (PSD, the executive branch of the Health and Safety Executive (HSE), a non-governmental public organization in Great Britain) defines an adjuvant as a substance other than water which is not itself pesticidally active but increases the effectiveness of a pesticide (http://www.hse.gov.uk/pesticides/topics/pesticide-approvals/pesticides-registration/applicant-guide/the-applicant-guide-adjuvan.htm). It refers here to REGULATION (EC) No 1107/2009 OF THE EUROPEAN PARLIAMENT AND OF THE COUNCIL of 21 Oct. 2009 concerning the placing of plant protection products on the market and repealing Council Directives 79/117/EEC and 91/414/EEC, Article 2 (3)(d). According to this, substances or preparations which consist of co-formulants or preparations containing one or more co-formulants. In the form in which they are supplied to the user and placed on the market to be mixed by the user with a plant protection product and which enhance its effectiveness or other pesticidal properties, are referred to as “adjuvants”. The terms “additives” or “adjuvants” are used synonymously in the present disclosure. Adjuvants used are frequently synthetic surfactants, for example ethoxylated alcohols, nonylphenol ethoxylates, alkyl polyglycosides or polyether-modified trisiloxanes.

The prior art biological crop protection formulations typically have multiple disadvantages. It is generally the case for all formulations of microbiological plant protection products that the microorganisms present lose viability and/or germinability with time. The formulations frequently have to be stored at temperatures below 10° C. in order to assure acceptable viability and/or germinability at least for a few weeks. Solid formulations such as WP and WG formulations additionally have the disadvantage that there is the risk of inhalation to the user when measuring-out and mixing the concentrated powder or granules. Moreover, solid formulations that are dispersed in water frequently exhibit reduced wetting of hydrophobic surfaces. Solid formulations additionally have the disadvantage of being poorly distributed in water and of being able to block the nozzles of the spray apparatus.

WO 2012/163322 A1 discloses a liquid preparation for biological plant protection, comprising a suspension of an active microorganism or a mixture of two or more active microorganisms or organs of microorganisms and a polyether-modified trisiloxane as carrier. This preparation is easy to handle and shows adequate storage stability. A disadvantage, however, is that the carrier is not biodegradable and does not consist of renewable raw materials, and that the atomization of the spray liquor gives rise to a large proportion of small droplets, such that the spray liquor is not applied accurately to the target substrate in windy conditions.

WO 2015/069708 A1 discloses a crop protection formulation comprising a carrier, a fungus as pesticide and a surface-active substance selected from sorbitan fatty acids, sorbitan ethoxylate ester, alcohol ethoxylates and combinations thereof. Paraffin oil is described as a preferred carrier. These crop protection formulations enable easier handling than solid formulations, but have the disadvantage of being nonbiodegradable.

WO 2017/210512 A1 discloses a nonaqueous, nonoily liquid carrier for living microorganisms. The carrier is preferably selected from the group consisting of polyethylene glycol, glycerol, ethylene glycol, dipropylene glycol, propylene carbonate and mixtures thereof. This carrier is easy to handle compared to solid formulations and shows adequate storage stability. A disadvantage, however, is that the carrier does not show good retention/adhesion on the plant, and the atomization of the spray liquor gives rise to a large proportion of small droplets, such that the spray liquor is not applied accurately to the target substrate in windy conditions.

WD 2016/055344 A1 discloses compositions comprising at least one hydrophobic, at least partly water-insoluble polyglycerol ester in combination with at least one emulsifier. What is specifically described is a mixture of 80% by weight of triglycerol trioleate with 20% by weight of polyethylene glycol-20 sorbitan trioleate. The composition is disclosed for enhancing the efficacy of pesticides and for avoidance of spray drift. It is also stated that the adhesion of sprays to plant surfaces is improved. The polyglycerol ester may be manufactured from natural raw materials and is biodegradable. In addition, the composition is self-emulsifying. However, there is no disclosure of the use of this composition as carrier for active microbiological ingredients.

There is therefore still a need to provide carrier compositions for active microbiological ingredients that have distinct advantages over the prior art. These carrier compositions are preferably to additionally act as adjuvants.

SUMMARY OF THE INVENTION

The problem addressed by the present invention was therefore that of providing novel carriers for active microbiological ingredients that overcome at least one disadvantage of the prior art.

A particular problem addressed was that of providing carriers for active microbiological ingredients that lead to improved handling and storability of the microbiological ingredients compared to the prior art. More particularly, an elevated biological efficacy of the active microbiological ingredient compared to the prior art is to be achieved. Thus, a particular problem addressed was that of conserving biological efficacy and/or bioavailability over a longer period compared to the prior art.

It has been found that, surprisingly, this problem is solved by the use of a composition including a polyglycerol ester and preferably an emulsifier as carrier for active microbiological ingredients.

For instance, the use of this carrier composition leads to elevated shelf life/storage stability of the active microbiological ingredients by comparison with water-dispersible powders or granules. By comparison with liquid carriers from the prior art, they surprisingly show very good adhesion of the droplets of the spray liquor on leaves. The carrier leads to good rain resistance of the crop protection formulation on the plants. The active microbiological ingredients are still thus present on the leaves and active even after rain. Moreover, the carrier has an anti-drift effect on the crop protection spray.

The spray droplets of the crop protection spray become larger and hence are less prone to drifting off during the spray operation. Moreover, the carrier is sustainably producible from renewable raw materials and also largely biodegradable. The carrier thus shows a particularly good profile of properties.

The problem addressed by the present invention is therefore solved by the subject-matter ng described. Advantageous configurations of the invention are specified in the examples and the description.

DETAILED DESCRIPTION OF THE INVENTION

The invention is described hereinafter by way of example, without any intention of limiting the invention to these illustrative embodiments. Where ranges, general formulae or classes of compounds are specified below, these are intended to encompass not only the corresponding ranges or groups of compounds which are explicitly mentioned but also all subranges and subgroups of compounds which can be obtained by removing individual values (ranges) or compounds. Any embodiment that can be obtained by combination of ranges/subranges and/or groups/subgroups, for example by combinations of inventive, essential, optional, preferred, preferable or preferably selected, further preferred, even further preferred, particularly preferred or especially preferred ranges/subranges and/or groups/subgroups, is fully incorporated into the disclosure-content of the present invention and is considered to be explicitly, directly and unambiguously disclosed. The expressions "preferably" and "preferentially" are used synonymously. The expressions "especially" and "especially preferably" are likewise used synonymously. Where documents are cited within the context of the present description, the entire content thereof is intended to be part of the disclosure-content of the present invention. In the case of compositions, the percentage figures, unless stated otherwise, are based on the overall composition. Where figures are given in percent hereinafter, these are percentages by weight unless stated otherwise. Where average values are reported hereinafter, these values are numerical averages unless stated otherwise. Where measurements or physical properties are reported hereinafter, unless stated otherwise, these are measurements or physical properties measured at 25° C. and preferably at a pressure of 101 325 Pa (standard pressure). The number-average molecular weight $M_N$ is determined by means of gel permeation chromatography (GPC) as per standard DIN 55672:2016, preferably as per standard DIN 55872-1:2016. Where numerical ranges in the form of "from X to Y" or "X to Y" are reported hereinafter, where X and Y are the limits of the numerical range, this is equivalent to the statement "from at least X up to and including Y", unless stated otherwise. Statements of ranges thus include the range limits X and Y, unless stated otherwise. Wherever molecules/molecule fragments have one or more stereocentres or can be differentiated into isomers on account of symmetries or can be differentiated into isomers on account of other effects, for example restricted rotation, all possible isomers are included by the present invention. Specific executions are defined hereinafter, and so features such as indices or structural constituents can be subject to restrictions by virtue of the execution. For all features unaffected by the restriction, the remaining definitions each remain valid. The word fragment "poly" encompasses in the context of this invention not just exclusively compounds having at least 2 repeating units of one or more monomers in the molecule, but preferably also those compositions of compounds having a molecular weight distribution and having an average molecular weight of at least 200 g/mol. This definition takes account of the fact that it is customary in the field of industry in question to refer to such compounds as polymers even if they do not appear to conform to a polymer definition as per OECD or REACH guidelines. The various fragments in the formulae (I) and (II) below may be distributed statistically. Statistical distributions may have a blockwise structure with any number of blocks and any sequence or they may be subject to a randomized distribution; they may also have an alternating structure or else form a gradient along the chain, if there is one; in particular, they can also form any mixed forms in which groups or different distributions may optionally follow one another. The formulae (I) and (II) describe compounds that may be constructed from repeat units, for example repeating fragments, blocks or monomer units, and may have a molar mass distribution. The frequency of the repeating units is reported by indices. The corresponding indices are the numerical average over all repeat units. The indices a, b and c used in the formulae should be regarded as statistical averages (number averages). The indices a, b and c used and also the value ranges of the reported indices are thus understood to be averages of the possible statistical distribution of the structures that are actually present and/or mixtures thereof. The polyglycerol esters to be used in accordance with the invention are preferably in the form of equilibrated mixtures. Specific embodiments may lead to restrictions to the statistical distributions as a result or the embodiment. There is no change in the statistical distribution for all regions unaffected by the restriction. Where documents are cited within the context of the present description, the entire content thereof is intended to be part of the disclosure-content of the present invention.

The present invention firstly provides for the use of a composition comprising (especially consisting essentially of) at least one polyglycerol ester and preferably at least one emulsifier as carrier for at least one active microbiological ingredient.

The composition comprising (especially essentially consisting of) at least one polyglycerol ester and preferably at least one emulsifier which is to be used as carrier is also referred to simply as carrier or carrier composition in the context of this disclosure. A composition comprising the carrier and the at least one active microbiological ingredient is referred to in the context of this disclosure as active ingredient composition.

The carrier composition is preferably liquid, it enables the dissolving, suspending or dispersing of the active microbiological ingredient, especially of fungi and/or fungal spores. The active microbiological ingredient is thus dissolved, suspended or dispersed in the carrier. The carrier additionally assists the dissolving, suspending or dispersing of the active microbiological ingredient in an aqueous composition, for example the spray liquor.

It is preferable that the at least one polyglycerol ester is at least partly water-insoluble and/or hydrophobic.

“Partly water-insoluble” means that the at least one polyglycerol ester at a given temperature in a concentration of at least 0.01 g/l up to 20 g/l in water already leads to turbidity perceptible to the human eye, and preferably forms two phases in a concentration of at least 0.5 g/l up to 2 g/l. Preferably, the solubility is determined at a temperature below 80° C. preferably below 70, 60, 50, 40, 30, 29, 28, 27, 26, 25, 24, 23, 22, 21 and below 20° C. In addition, the solubility is determined preferably above 0° C. more preferably above 5, 10, 15, 16, 17, 18, 19, 20, 21, 22, 23, 24 and above 25° C. More preferably, the solubility is determined at ambient temperature. Especially preferably, the solubility is determined between 15° C. and 30° C., more preferably from 20° C. up to 25° C.

A measure employed for hydrophobicity may, for example, be the HLB (hydrophillic lipophilic balance) value. It is preferable that the at least one polyglycerol ester has an HLB value of less than 8, preferably of 1 to 7, especially of 2 to 6.5. The HLB value can be determined by various prior art methods and is a recognized measure of hydrophobicity. The HLB value is preferably determined by the Griffin method (W. C. *Griffin: Classification of surface active agents by HLB, J. Soc. Cosmet. Chem.* 1, 1949, p. 311-326). The HLB value is calculated here by the formula $$HLB = 20 \cdot \left(1 - \frac{m_1}{m}\right)$$

where $m_1$ is the molar mass of the lipophilic component of a molecule and m is the molar mass of the entire molecule. The molar masses are determined by prior art methods; they are preferably determined by mass spectrometry; the lipophilic component is determined from the mass spectrometry results using the stoichiometric principles known to the person skilled in the art. The molar masses can also be calculated from the molecular structure.

The polyglycerol ester preferably has an HLB value of not more than 8, preferably not more than 7, especially not more than 6.5. Further preferably, the HLB value is at least 0.5, preferably at least 1 and especially at least 2, it is therefore also preferable that the at least one polyglycerol ester has an HLB value of 0.5 to 8, preferably of 1 to 7, especially of 2 to 6.5.

It is preferable that the acyloxy radicals (also referred to as alkanoyloxy radicals) of the at least one polyglycerol ester have 4 to 40, preferably 8 to 22 and especially 10 to 18 carbon atoms.

It is additionally preferable that the at least one polyglycerol ester is a compound of the general formula (I)

$M_a D_b T_c$ Formula (I);

with:

$M=[C_3H_5(OR)_2O_{1/2}]$;

$D=[C_3H_5(OR)_1O_{2/2}]$;

$T=[C_3H_5O_{3/2}]$;

a=1 to 10, preferably 2 to 3, especially 2;

b=0 to 10, preferably greater than 0 to 5, especially 1 to 3;

c=0 to 3, preferably 0 to 1, especially 0;

with the proviso that:

a+b+c=2 to 20, preferably 2 to 4, especially 3;

where the R radicals are each independently selected from the group consisting of acyl radicals R'—C(=O)— and H, with the proviso that at least one R radical is not H;

where the R' radicals are each independently selected from the group consisting of monovalent aliphatic, saturated or unsaturated hydrocarbon radicals having 3 to 39, preferably 7 to 21 and especially 9 to 17 carbon atoms.

Preferably, with regard to the units M, D and T:

M = 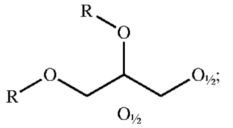

D = 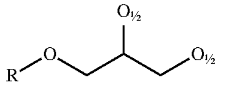 and 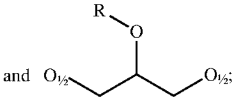

T = 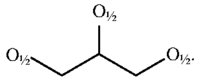

It is further preferable that the at least one polyglycerol ester is a compound of the general formula (II)

Formula (II)

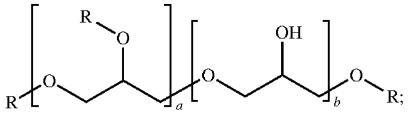

where a=1 to 10, preferably 2 to 3, especially 2;

b=0 to 10, preferably greater than 0 to 5, especially 1 to 3;

with the proviso that:

a+b=2 to 20, preferably 2 to 4, especially 3;

where the R radicals are each independently selected from the group consisting of acyl radicals R'—C(═O)— and H, with the proviso that at least one R radical is not H;

where the R' radicals are each independently selected from the group consisting of monovalent aliphatic, saturated or unsaturated hydrocarbon radicals having 3 to 39, preferably 7 to 21 and especially 9 to 17 carbon atoms.

Preferably, the polyglycerol esters of the compositions according to the invention have more than one R radical of the R'—C(═O)— form, more preferably at least 2, even more preferably at least 3.

The R radicals of the R'—C(═O)— form are preferably the acyl radicals of saturated or unsaturated fatty acids, where the fatty acids have 4 up to 40 carbon atoms, more preferably butyric acid (butanoic acid), caproic acid (hexanoic acid), caprylic acid (octanoic acid), capric acid (decanoic acid), lauric acid (dodecanoic acid), myristic acid (tetradecanoic acid), palmitic acid (hexadecanoic acid), stearic acid (octadecanoic acid), arachic acid (eicosanoic acid), behenic acid (docosanoic acid), lignoceric acid (tetracosanoic acid), palmitoleic acid ((Z)-9-hexadecenoic acid), oleic acid ((Z)-9-hexadecenoic acid), elaidic acid ((E)-9-octadecenoic acid), cis-vaccenic acid ((Z)-11-octadecenoic acid), linoleic acid ((9Z,12Z)-9,12-octadecadienoic acid), alpha-linolenic acid ((9Z,12Z,15Z)-9,12,15-octadecatrienoic acid), gamma-linolenic acid ((6Z,9Z,12Z)-8,9,12-octadecatrienoic acid), di-homo-gamma-linolenic acid ((8Z, 11Z,14Z)-8,11,14-eicosatrienoic acid), arachidonic acid ((5Z,8Z,11Z,14Z)-5,8,11,14-eicosatetraenoic acid), erucic acid ((Z)-13-docosenoic acid), nervonic acid ((Z)-15-tetracosenoic acid), ricinoleic acid, hydroxystearic acid and undecylenic acid, and also mixtures thereof, for example rapeseed oil acid, soya fatty acid, sunflower fatty acid, peanut fatty acid and tall oil fatty acid. Particular preference is given here to radicals of oleic acid.

In the calculation of the HLB value, the molar mass of the lipophilic molecular moiety is found from the arithmetic average of the sum total of the molar masses of all R' radicals present in the molecule as parts of the acyl radicals R'—C(═O)—.

Sources of suitable fatty acids or fatty acid esters, in particular glycerides, can be vegetable or animal fats, oils or waxes. For example, it is possible to use: pork lard, beef tallow, goose fat, duck fat, chicken fat, horse fat, whale oil, fish oil, palm oil, olive oil, avocado oil, seed kernel oils, coconut oil, palm kernel oil, cocoa butter, cottonseed oil, pumpkinseed oil, maize kernel oil, sunflower oil, wheatgerm oil, grapeseed oil, sesame oil, linseed oil, soybean oil, peanut oil, lupin oil, rapeseed oil, mustard oil, castor oil, jatropha oil, walnut oil, jojoba oil, lecithin, for example based on soya, rapeseed or sunflowers, bone oil, neatsfoot oil, borage oil, lanolin, emu oil, deer tallow, marmot oil, mink oil, safflower oil, hemp oil, pumpkin oil, evening primrose oil, tall oil, and also carnauba wax, beeswax, candelilla wax, ouricury wax, sugarcane wax, retamo wax, caranday wax, raffia wax, esparto wax, alfalfa wax, bamboo wax, hemp wax, Douglas fir wax, cork wax, sisal wax, flax wax, cotton wax, dammar wax, tea wax, coffee wax, rice wax, oleander wax or wool wax.

Particular preference is given to the polyglycerol ester compounds of the formulae (I) or (II) having an arithmetic average of 2.9 to 3.1 radicals of the R'—C(═O)— form and an HLB value of 4 to 6.5.

Particular preference is additionally given to the polyglycerol ester compounds of the formula (II) where the sum of a+b is 3 and which have an arithmetic average of 2.9 to 3.1 radicals of the R'—C(═O)— form and an HLB value of 4 to 6.5.

Particular preference is additionally given to the polyglycerol ester compounds of the formula (II) which have an arithmetic average of 2.9 to 3.1 radicals of the R'—C(═O)— form and an HLB value of 4 to 6.5, where the acyl radicals are of fatty acid mixtures containing oleic acid, stearic acid, palmitic acid and gamma-linolenic acid and where said fatty acids preferably account for at least 85% by weight in the fatty acid mixture.

Particular preference is given to the polyglycerol ester compounds of the formula (II) which have an arithmetic average of 2.9 to 3.1 radicals of the R'—C(═O)— form and an HLB value of 4 to 6.5, where the acyl radicals originate from fatty acid mixtures containing oleic acid, stearic acid, palmitic acid and gamma-linolenic acid and where said fatty acids preferably account for at least 85% by weight in the fatty acid mixture.

Especial preference is given to the polyglycerol ester compounds of the formula (II) which have an arithmetic average of 2.9 to 3.1 radicals of the R'—C(═O)— form and an HLB value of 4 to 6.5, where the proportion by mass of oleyl radicals is at least 75%, preferably 85%, especially 95%, based on the mass of all acyl radicals.

It is particularly preferable that the at least one polyglycerol ester is triglycerol trioleate.

Preferably, the at least one polyglycerol ester or the carrier comprising the at least one polyglycerol ester and preferably the at least one emulsifier has a biodegradability of at least 50%, preferably at least 55%, especially at least 60%, when a maximum biodegradability value is 100%.

It is preferable that the carrier additionally contains at least one emulsifier. However, the carrier need not necessarily contain at least one emulsifier.

The emulsifier is different from the at least one polyglycerol ester. The emulsifier is preferably selected from the group consisting of: fatty acid esters of polyhydric alcohols and their polyalkylene glycol derivatives, polyglycol derivatives of fatty acids and fatty alcohols, sorbitan fatty acid esters and ethoxylated and/or propoxylated sorbitan fatty acid esters, alkylphenol ethoxylates, block copolymers of ethylene oxide and propylene oxide, ethoxylated and/or propoxylated amines, amine oxides, acetylenediol surfactants and ethoxylated and/or propoxylated acetylenediols, silicone surfactants.

Even more preferably, the at least one emulsifier is selected from the group consisting of sorbitan fatty acid esters and ethoxylated sorbitan fatty acid esters, preferably ethoxylated sorbitan fatty acid esters.

It is further preferable that the acyloxy radicals of the at least one sorbitan fatty acid ester or ethoxylated sorbitan fatty acid ester have 4 to 40, preferably 8 to 22 and especially 10 to 18 carbon atoms and/or that the at least one sorbitan fatty acid ester or ethoxylated sorbitan fatty acid ester has 0 to 40, preferably 10 to 30 and especially 15 to 25 oxyethylene groups.

The fatty acids and fatty acid radicals of the sorbitan fatty acid esters are preferably defined in the same way as the fatty acids or fatty acid radicals of the polyglycerol esters. Preferably, the acyl radicals (also referred to as alkanoyl radicals) originate from fatty acid mixtures comprising oleic acid, stearic acid, palmitic acid and gamma-linolenic acid, where said fatty acids preferably account for at least 85% by weight in the fatty acid mixture. Especially preferred are ethoxylated sorbitan fatty acid esters, wherein the proportion by mass of oleyl radicals is at least 75%, preferably 85%, especially 95%, based on the mass of all acyl radicals.

It is preferable that the at least one emulsifier has an HLB value of not less than 9, preferably of not less than 10, especially of not less than 11. Further preferably, the HLB value is not more than 16, preferably not more than 15, especially not more than 13. It is therefore also preferable that the at least one emulsifier has an HLB value of 9 to 16, preferably of 10 to 15, especially of 11 to 13. The HLB value is determined as described above. The HLB value of the sorbitan fatty acid esters and/or ethoxylated sorbitan fatty acid esters is preferably determined as for the polyglycerol esters. The molar mass of the lipophilic molecular moiety is found from the arithmetic average of the sum total of the molar masses of all R' radicals present in the molecule as part or the acyl radicals R'—(CO)—.

The R' radicals are preferably as defined for the polyglycerol esters. The R' radical as part of an acyl radical R'—(CO)— of the sorbitan fatty acid ester or ethoxylated sorbitan fatty acid ester is preferably selected here from the group consisting of monovalent aliphatic, saturated or unsaturated hydrocarbon radicals having 3 to 39, preferably 7 to 21 and especially 9 to 17 carbon atoms. Calculation of the molar mass of the overall molecule is conducted as defined above.

It is particularly preferable that the at least one emulsifier is polyethylene glycol-20 sorbitan trioleate. The number 20 Indicates the average number of ethylene oxide units in the polyethylene glycol radical.

The HLB values of the at least one polyglycerol ester and the at least one emulsifier are preferably matched to one another. It is preferable that the polyglycerol ester has an HLB value of not more than 8, preferably not more than 7, especially not more than 6.5, and the at least one emulsifier has an HLB value of not less than 9, preferably of not less than 10, especially of not less than 11. It is further preferable that the at least one polyglycerol ester has an HLB value of 0.5 to 8, preferably of 1 to 7, especially of 2 to 6.5, and the at least one emulsifier has an HLB value of 9 to 16, preferably of 10 to 15, especially of 11 to 13.

It is especially preferable that the at least one polyglycerol ester is triglycerol trioleate and the at least one emulsifier is polyethylene glycol-20 sorbitan trioleate. The combination of triglycerol trioleate and polyethylene glycol-20 sorbitan trioleate shows particularly advantageous properties as a carrier for an active microbiological ingredient.

The carrier preferably consists predominantly of the at least one polyglycerol ester and, if additionally present, the at least one emulsifier. It is preferable that the proportion by mass of the at least one polyglycerol ester together with the any at least one emulsifier additionally present is at least 90%, preferably at least 95%, especially at least 99%, based on the total mass of the carrier. It is particularly advantageous when the composition used as carrier consists (essentially) of the at least one polyglycerol ester and optionally additionally the at least one emulsifier.

Preferably, the proportion by mass of the at least one polyglycerol ester based on the total mass of the carrier composition is 60% to 100%, preferably 70% to 90%, especially 75% to 85%; and the proportion by mass of any at least one emulsifier additionally present based on the total mass of the carrier composition is 0% to 40%, preferably 10% to 30%, especially 15% to 25%. Preferably, the carrier composition consists essentially of the at least one polyglycerol ester and optionally additionally the at least one emulsifier.

It is further preferable that the carrier contains the at least one polyglycerol ester in a proportion by mass based on the total mass of the carrier composition of 60% to 100%, preferably of 70% to 90%, especially of 75% to 85%, and that the carrier contains, as the at least one emulsifier, at least one sorbitan fatty acid ester and/or at least one ethoxylated sorbitan fatty acid ester, preferably at least one ethoxylated sorbitan fatty acid ester, in a proportion by mass based on the total mass of the carrier composition of 0% to 40%, preferably of 10% to 30%, especially of 15% to 25%.

It is further preferable that the carrier contains, as polyglycerol ester, triglycerol trioleate in a proportion by mass based on the total mass of the carrier composition of 60% to 100%, preferably of 70% to 90%, especially of 75% to 85%, and that the carrier contains, as emulsifier, polyethylene glycol-20 sorbitan trioleate in a proportion by mass based on the total mass of the carrier composition of 0% to 40%, preferably of 10% to 30%, especially of 15% to 25%.

It is further preferable that the carrier consists essentially of the at least one polyglycerol ester in a proportion by mass based on the total mass of the carrier composition of 60% to 100%, preferably of 70% to 90%, especially of 75% to 85%, and the at least one emulsifier selected from the group consisting of sorbitan fatty acid esters and ethoxylated sorbitan fatty acid esters, preferably ethoxylated sorbitan fatty acid esters, in a proportion by mass based on the total mass of the carrier composition of 0% to 40%, preferably of 10% to 30%, especially of 15% to 25%.

It is even further preferable that the carrier consists essentially of triglycerol trioleate in a proportion by mass based on the total mass of the carrier composition of 60% to 100%, preferably of 70% to 90%, especially of 75% to 85%, and polyethylene glycol-20 sorbitan trioleate in a proportion by mass based on the total mass of the carrier composition of 0% to 40%, preferably of 10% to 30%, especially of 15% to 25%.

It is preferable that the active microbiological ingredient is selected from the group consisting of microorganisms, organs of microorganisms and mixtures thereof. It is especially preferable that the microorganism is living and/or active.

It is further preferable that the active microbiological ingredient has a preferably antagonistic and/or hyperparasitic effect directed against a particular pathogen, preferably plant pathogen.

It is preferable that the active microbiological ingredient is selected from the group consisting of acaricides (AC), bactericides (BA), fungicides (FU), herbicides (HE), insecticides (IN), nematicides (NE), growth regulators (PG), plant fortifiers (PS), biostimulants, inoculates or mixtures thereof. Some of these active biological ingredients are specified, for example, in *The Manual of Biocontrol Agents,* 2001, The British Crop Protection Council. However, the present invention is not limited solely to these active ingredients listed therein.

Preferably, the active microbiological ingredient increases resistance and/or stress tolerance and/or nutrient availability in plants.

The microorganisms in the context of the present disclosure include bacteria, fungi, algae, protozoa and viruses.

The microorganisms are accordingly selected from the group consisting of bacteria, fungi, algae, protozoa, viruses and mixtures thereof.

The microorganism is preferably selected from the group consisting of fungi and bacteria.

In a preferred embodiment, the microorganism is not selected from the group of viruses, especially not from the group consisting of viruses, algae and protozoa.

In a preferred embodiment, the active microbiological ingredient is selected from the group consisting of fungi, fungal organs, bacteria, bacterial organs and mixtures thereof.

In a preferred embodiment, the active microbiological ingredient is selected from the group consisting of fungi, fungal organs and mixtures thereof.

It is further preferable that the fungal organs are selected from the group consisting of spores, conidia, blastospores, chlamydospores, sclerotia, hyphal segments and mixtures thereof.

Further preferably, the active microbiological ingredient is selected from the group consisting of the fungi *Ampelomyces quisqualis, Aureobasidium pullulans, Beauveria bassiana, Beauveria brongniartii, Candida oleophila, Clonostachys rosea, Conlothyrium minitans, Gliocladium catenulatum, Gliocladium virens, Isaria fumosorosea, Isaria* spp., *Laetisaria arvalis, Lecanicillium lecanii, Lecanicillium muscarium, Metarhizium anisopliae, Myrothecium verrucaria, Metarhizium rileyi* (*Nomuraea rileyi*), *Paecilomyces lilacinus, Phlebiopsis gigantea, Phoma macrostoma, Purpureocillium lilacinus, Pythium oligandrum, Talaromyces flavus, Teratospema oligociadum, Trichoderma asperellum, Trichoderma atroviride, Trichoderma gamsii, Trichoderma hamatum, Trichoderma harzianum, Trichoderma koningii, Trichoderma reesei, Trichoderma* spp., *Verticillium biguttatum*, their fungal organs, and mixtures of these fungi and/or fungal organs.

More preferably, the active microbiological ingredient is selected from the group consisting of the fungi *Ampelomyces quisqualis, Aureobasidium pullulans, Beauveria bassiana, Candida oleophila, Clonostachys rosea, Coniothyrium minitans, Gliocladium virens, Isaria fumosorosea, Lecanicillium muscarium, Metarhizium anisopliae, Myrothecium verrucaria, Metarhizium rileyi* (*Nomuraea rileyi*), *Purpureocillium lilacinus, Phlebiopsis gigantea, Trichoderma asperellum, Trichoderma atroviride, Trichoderma gamsii, Trichoderma hamatum, Trichoderma harzianum, Onchocerca koningii, Trichoderma reesei*, their fungal organs, and mixtures of these fungi and/or fungal organs.

Particular preference is given to the use of the following fungi having antagonistic and/or hyperparasitic action against particular plant pathogens: *Ampelomyces quisqualis, Beauveria bassiana, Beauveria brongniartii, Clonostachys rosea, Coniothyrium minitans, Gliocladium catenulatum, Isaria* spp., *Laetisaria arvalis, Lecanicillium lecanii, Lecanicillium muscarium, Metarhizium anisopliae, Metarhizium rileyi* (*Nomuraea rileyi*), *Paecilomyces lilacinus, Phoma macrostoma, Pythium oligandrum. Talaromyces flavus, Teratosperma oligociadum, Trichoderma* spp. and *Verticillium biguttatum.*

Fungi used with preference that improve nutrient availability in the soil or increase the resistance of the plants to stress factors (including pathogens and pests) are: *Penicillium bilaii, Trichoderma* spp. and all species that can be classified in the group of the *Mycorrhiza* fungi.

Active microbiological ingredients selected from the group consisting of fungi, fungal organs and mixtures thereof are particularly suitable for use as plant protection product, for use as biostimulant and/or for treatment of seed.

In a further preferred embodiment, the active microbiological ingredient is a bacterium or a mixture of various bacteria.

In a further preferred embodiment, the bacterium or the mixture of various bacteria is selected from the group consisting of *Azospirillum brasilense, Azotobacter chroococcum, Bacillus amyloliquefaciens, Bacillus firmus, Bacillus licheniformis, Bacillus mycoides, Bacillus pumilus, Bacillus subtills, Bacillus thuringiensis, Bradyrhizobium* spp., *Burkholderia* spp., *Chromobacterium subtsugae, Gluconacetobacter* spp., *Pseudomonas chlororaphis, Pseudomonas fluorescens, Pseudomonas syringae, Rhizobium* spp., *Streptomyces griseoviridis, Streptomyces lydicus* and mixtures thereof. These compositions are particularly suitable for use as plant protection products, for use as biostimulant and/or for treatment of seed.

In a further preferred embodiment, the bacterium or the mixture of various bacteria is selected from the group consisting of *Lactobacillus gasseri, Lactobacillus paracasei, Lactobacillus plantarum, Lactobacillus crispatus, Lactobacillus casei, Lactobacillus animalis, Lactobacillus rhamnosus, Lactobacillus pentosus, Lactobacillus reuteri, Lactococcus lactis, Bacillus pumilus, Bacillus licheniformis, Bacillus coagulans, Bacillus cereus, Bacillus subtills, Bacillus amyloliquefaciens, Clostridium butyricum, Enterococcus faecium, Streptococcus faecium, Lactobacillus acidophilus, Lactobacillus salivarius, Lactobacillus fermentum, Lactobacillus johnsonii, Lactobacillus helveticus, Streptococcus thermophiles, Pediococcus acidilactici, Bifidobacterium lactis, Bifidobacterium adolescentis, Bifidobacterium lactobacillus, Bifidobacterium animalis, Bifidobacterium longum, Bifidobacterium infantis* and mixtures thereof. These compositions are particularly suitable for use as probiotic in foods and/or animal feeds.

In a further preferred embodiment, the active microbiological ingredient is selected from the group consisting of lactobacilli, bifidobacteria, *Enterococcus faecalis, Enterococcus faecium* and the yeast fungi *Saccharomyces boulardii* and *Saccharomyces cerevisiae* and mixtures thereof. These compositions may be suitable, for example, for use as probiotic medicament. For some disorders and fields of use, the efficacy of probiotic medicaments is comparatively well-researched. These include various chronic inflammatory bowel disorders, various diarrhoeal disorders, chronic constipation, prevention of allergies and infections in premature babies, prevention of neurodermatitis, infections of the throat, nose, ears, urinary tract infections and dental caries.

In a further preferred embodiment of the composition, the active microbiological ingredient is a virus or a mixture of different viruses, preferably selected from the group of the baculoviruses, further preferably from the nucleopolyhedrovirus and granulovirus genera. In a preferred embodiment of the composition, the active microbiological ingredient selected is the CpGV virus (*Cydia pomonella* granulovirus). This virus is used, for example, for protection from codling moth caterpillars in pomiculture. In a further preferred embodiment of the composition, the active microbiological ingredient selected is the HearNPV virus (*Helicoverpa armigera* nucleopolyhedrovirus). This virus acts specifically against the larvae of the cotton bollworm and is used, for example, for protection of cotton plants.

It is also preferred in accordance with the Invention that the active microbiological ingredient is a mixture of the abovementioned microorganisms and/or organs thereof.

It is further preferable that the at least one active microbiological ingredient is selected from the group consisting of

*Trichoderma harzianum, Bacillus amyloliquefaciens, Beauveria bassiana, Metarhizium rileyi* (*Nomuraea rileyi*), *Metarhizium anisopliae, Clonostachys rosea, Aureobasidium pullulans, Coniothyrium minitans* and their organs, where the organs are preferably selected from the group consisting of spores, conidia, blastospores, chlamydospores, sclerotia and hypha segments.

It is further preferable that the at least one active microbiological ingredient comprises spores, preferably fungal spores and/or bacterial spores, especially spores of *Trichoderma harzianum* and/or of *Bacillus amyloliquefaciens* and/or of *Beauveria bassiana* and/or of *Metarhizium rileyi* (*Nomuraea rileyi*) and/or of *Metarhizium anisopliae* and/or of *Clonostachys rosea* and/or of *Aureobasidium pullulans* and/or of *Coniothyrium minitans*.

It is more preferable that the at least one active microbiological ingredient is selected from the group consisting of *Trichoderma harzianum* and spores of *Trichoderma harzianum*.

It is particularly preferable that the at least one active microbiological ingredient is spores of *Trichoderma harzianum*. It is thus particularly preferable that the at least one active microbiological ingredient comprises or consists of spores of *Trichoderma harzianum*.

It is also preferable that the active microbiological ingredient comprises vegetative cells, especially vegetative cells of *Pseudomonas fluorescens* and/or *Pseudomonas chlororaphis*.

The adjustment of the activity of water increases the viability and/or germinability of the active microbial ingredient present and hence also the storability (shelf life) thereof. The activity of water ($a_w$) is a thermodynamic parameter. It is a measure of the amount of water available for chemical, biochemical and microbial reactions in samples, for example aqueous solutions and food/drink compositions, and can also be used to characterize the carrier compositions. Activity of water is reported as the $a_w$ value and is defined as the ratio or the water vapour pressure above the sample (p) to the water vapour pressure of pure water ($p_0$) at the same temperature, $a_w=p/p_0$. The activity of water corresponds to 1/100 of the relative equilibrium humidity (REH). Relative equilibrium humidity is also referred to as equilibrium relative humidity (ERH). Pure water has an $a_w$ of 1, and any addition of water-binding substances results in lowering of the $a_w$ below 1. It is preferable that the $a_w$ of the carrier composition is less than 0.4, preferably less than 0.3, especially less than 0.25. Methods of determining the $a_w$ value are known to the person skilled in the art. The $a_w$ value is preferably determined as described in the examples.

As a result of the synthesis, polyglycerol esters may contain residual amounts of water, it may therefore be advantageous to adjust, especially to reduce, the water content and hence the activity of water. This can be accomplished, for example, by means of a thermal separation process. Thermal separation processes are known by this term to those skilled in the art and include all processes based on the establishment of a thermodynamic phase equilibrium. Preferred thermal separation processes are selected from the group consisting of distillation, rectification, adsorption, crystallization, extraction, absorption, drying and freezing-out, particular preference being given to methods of distillation and rectification. For drying, it is also possible to use desiccants such as molecular sieves, for example zeolites.

The inventive use of the carrier composition leads here to an increase in storage stability of the active microbiological ingredient. Preferably, the storage stability is determined as described in the examples.

It is therefore further preferable that the proportion of viable spores or vegetative cells after storage, determined as described in the examples, after 28 days is at least 6%, further preferably at least 8%, especially at least 10%, based on the starting value.

The invention therefore further provides for the inventive use of the carrier composition for increasing the storage stability of the active microbiological ingredient.

The invention therefore still further provides a method of increasing the storage stability of at least one active microbiological ingredient by using a composition comprising at least one polyglycerol ester and preferably at least one emulsifier.

The above remarks are applicable to the carrier, the at least one polyglycerol ester, the at least one emulsifier and the active microbiological ingredient. All definitions, embodiments and elucidations applicable to the inventive use are thus also applicable mutatis mutandis to the method according to the invention and vice versa.

The invention further provides a composition (also referred to as active ingredient composition) comprising (a) a carrier comprising (a1) at least one polyglycerol ester and preferably (a2) at least one emulsifier, and (b) at least one active microbiological ingredient.

The above remarks are applicable to the carrier, the at least one polyglycerol ester, the at least one emulsifier and the active microbiological ingredient. All definitions, embodiments and elucidations which are applicable to the inventive use and/or the inventive method are thus also applicable mutatis mutandis to the composition (active ingredient composition) according to the invention, and vice versa.

The active ingredient composition may be free from component (a2), but it is preferable for the active ingredient composition to contain the component (a2).

It is preferable that the active ingredient composition consists (essentially) of components (a1) and (b), more preferably of components (a1), (a2) and (b).

It is further preferable that the proportion by mass of the carrier, based on the total mass or the active ingredient composition, is 40% to 99%, preferably 70% to 99%, especially 80% to 99%.

It is further preferable that the proportion by mass of the at least one active microbiological ingredient, based on the total mass of the active ingredient composition, is 1% to 60%, preferably 1% to 30%, especially 1% to 20%.

It is therefore preferable that the proportion by mass of the carrier based on the total mass of the active ingredient composition is 40% to 99%, preferably 70% to 99%, especially 80% to 99%, and that the proportion by mass of the at least one active microbiological ingredient based on the total mass of the active ingredient composition is 1% to 60%, preferably 1% to 30%, especially 1% to 20%.

It is further preferable that the ratio of the mass of the carrier composition to the mass of the at least one active microbiological ingredient is from 1:1 to 20:1, preferably from 3:1 to 15:1, especially from 5:1 to 10:1.

Preferably, the $a_w$ value of the active ingredient composition is likewise less than 0.4, preferably less than 0.3, especially less than 0.25. The $a_w$ value is preferably determined here as for the carrier.

It is further preferable that the active ingredient composition is in liquid form, i.e. for example, in the form of an oil dispersion (OD), dispersion concentrate (DC) or suspension concentrate (SC). This has the advantage that the composition is easy to handle. But it is also possible that the active ingredient composition is solid, i.e., for example, is in the form of a wettable powder (WP) or of water-dispersible granules (WG).

The active ingredient composition is obtainable by mixing the active microbiological ingredient with the carrier. It is preferable that the active microbiological ingredient is dissolved and/or suspended and/or dispersed in the carrier. The active microbiological ingredient is preferably cultivated here beforehand on a nutrient medium suitable for the purpose by methods known per se, for example submerged fermentation or solid fermentation. Preferably, the cultivated microorganism is processed by suitable separation, drying, grinding and/or dispersion methods. Preferably, after the cultivation, the microorganism and/or its organs that are used with preference are preferably separated from the culture substrate. In a particularly preferred variant, the culture substrate over which the microorganism has grown (especially in the case of use of solid culture substrates) is dried beforehand. In another variant, the microorganism or its organs used with preference, after they have been separated from the culture substrate, can be dried, for example, with the aid of freeze-drying or spray-drying methods. After the separation and any drying, the microorganism and/or its organs are suspended and/or dispersed in the carrier. It is further preferable that the microorganism, preferably selected from the group of the fungi, is processed by grinding and/or dispersing methods. In this case, the cultivation is followed, prior to the separation of the microorganism and/or its organs that are used with preference, by processing of the culture substrate on which they have grown by a suitable dispersion method or, after drying, by a suitable grinding method. Preferably, there is then a subsequent separation/isolation of the microorganism or of its organs that are used with preference by methods known per se, such as sieving, filtration, windsifting, decanting and/or centrifugation methods. Preferably, the active ingredient composition is produced by mixing the at least one microorganism and/or its organs into the carrier, preferably in a mixing tank using a stirrer. This preferably affords a liquid active ingredient composition, for example an oil dispersion (OD), suspension concentrate (SC) or dispersion concentrate (DC). By selection of suitable polyglycerol esters and/or use of appropriate viscosity regulators, it is possible to adjust the viscosity such that at least only a reduced separation, if any, of the microorganisms that have been mixed into the liquid formulation, preferably an SC and DC formulation, can be observed.

The active ingredient composition is preferably diluted with water in the spray tank to give a spray liquor for application to plants or the soil. The proportion by mass of the water based on the total mass of the spray liquor is preferably 80% to 99.99%, preferably 90% to 99.9%, especially 95% to 99%. Alternatively, the proportion by mass may be higher or lower, according to the application rate of the active microbiological ingredient. The spray liquor should preferably be sprayed at a maximum of 1000 litres, preferably 50 litres to 600 litres, especially at 100 litres to 400 litres, of water per hectare, which is guided by the application rate of the active microbiological ingredient and by the type and number of plants.

The active ingredient composition shows a high microbe count on dilution of the composition in the spray tank. It is therefore further preferable that the microbe count, determined as described in the examples, is at least 50%, preferably at least 70%, especially at least 90%, based on the starting value.

The present invention further provides for the use of the active ingredient composition according to the invention for the treatment of plants and/or of seed and/or of soils, and/or for use as biostimulant.

Preferably, the active ingredient composition according to the invention is used as biological plant protection product, biological plant fortification product or biological soil improvement product; more preferably, the active ingredient composition according to the invention is used for plant protection.

In the case of use for plant protection, for the treatment of seed and/or as a biostimulant, the active ingredient composition is preferably mixed or watered into the soil or applied to the plant or to the seed. According to the intended end use, the active ingredient composition here is optionally diluted with water to the use concentration.

Preferably, the active ingredient compositions according to the invention are used as formulation, preferably as plant protection formulation, for spray liquors. Preferably, the proportion by mass here of the carrier based on the total mass of the spray liquor is from 0.001% to 1%, further preferably from 0.01% to 0.5%.

Preferably, the spray liquor is applied to the plant via an irrigation system selected from the group consisting of micro-irrigation systems, sprinkler systems and drip systems.

For their use on plants or plant parts, plant protection formulations are, in most cases, diluted with water before the usual spraying through nozzles, and contain, besides the active component, other adjuvants too, such as emulsifiers, dispersing aids, antifreeze agents, antifoams, biocides and surface-active substances such as surfactants. Active substances, especially fungicides, insecticides and nutrients, alone or In combination and having been provided with the other auxiliaries specified above, can also be applied by various methods to seeds (seed) of plants. Such methods are also referred to as seed treatment methods. The treatment of seed with fungicides and insecticides can protect plants in the early stage of growth from diseases and attack by insects.

The plant protection formulations can also be applied to the plants by means of insects that pollinate plants, called “pollinators”, for example bumblebees or bees. The composition here is optionally diluted with water to the use concentration. But preference is given to using the composition undiluted. The spreading of chemical plant protection products by means of pollinating insects is described, for example, in WD 2011026983 A1. Biological plant protection products can also be spread in a corresponding manner, it is advantageous here when the pollinators are not impaired or damaged by the active microbiological ingredient or the composition.

If biocides are employed in the formulations, they are selected such that they are not harmful to the microorganisms of the compositions according to the invention. This means that the microorganisms in the formulation are restricted only to a minor degree, if at all, in their viability and/or germinability. Preferably, viability and/or germinability is maintained to an extent or at least 80%, preferably at least 90%, more preferably to an extent of at least 95%, 2 hours after the formulation has been made up. Analysis is effected as described in the examples.

An active ingredient composition containing conidia of *Paecilomyces lilacinus* as active microbial ingredient can be used for the biological control of phytoparasitic nematodes. When spores of *Talaromyces flavus* are used, the preparation can be used for control of *Verticillium dahliae*, a pathogen that causes economically relevant wilting in cotton. Compositions containing spores of *Metarhizium rileyi* (*Nomuraea rileyi*) can be used to control the caterpillars of various damaging butterfly species, for example *Helicoverpa armigera* and *Spodoptera exigua*. The employment of the composition using conidia of *Penicillium bilaii* increases the availability of mineral phosphorus in the soil.

Preferred agricultural fields of use of the active ingredient compositions are arable farming, growing of garden and ornamental plants, viticulture and cotton growing. Particular preference is given to fruit and vegetable growing. Preferred fruit is pome fruit, stone fruit, berry fruit and shelled fruit. Preferred vegetables are root vegetables, shoot vegetables, tuber vegetables, onion-type vegetables, leafstalk vegetables, leaf vegetables, leaf lettuces, seed vegetables and fruit vegetables.

In the case of use of the active ingredient composition i) for the treatment or plants; or ii) for the treatment of seed; or iii) for the treatment of soils; or iv) as biostimulant;

the active ingredient composition is preferably used as a formulation for spray liquors, where the proportion by mass of the carrier composition based on the total mass of the spray liquor is 0.001% to 1%.

The present invention further provides for the use of the active ingredient composition as probiotic food supplement and/or probiotic animal feed additive. The active ingredient compositions may be used as probiotic in foods and/or animal feeds. Probiotic foods and/or animal feeds typically contain bacteria and/or fungi as active microbial ingredient. The probiotic foods include, for example, yoghurt preparations, kefir preparations, soured milk preparations and vegetables fermented in soured milk. The active microbial ingredient here displays a health-promoting effect in the intestine.

The present invention further provides an active ingredient composition according to the invention for use as probiotic medicament.

The carrier compositions and active ingredient compositions have numerous advantages: One advantage is the improvement in the storability of microorganisms through use of the carrier composition or improved storability of the active ingredient composition. More particularly, the active ingredient composition can be stored at room temperature for many weeks. This simplifies transport and storage. The composition is stored and transported, preferably with exclusion of air, in bottles, pouches, canisters or drums that have been sealed airtight. The elevated storability especially leads to an increase in biological activity.

Furthermore, the active ingredient composition, especially in the form of a dispersion concentrate or suspension concentrate, shows improved viability and/or germinability compared to the prior art.

A further improvement over the prior art is that the microorganisms and/or their organs remain viable and/or germinable for much longer in the ready-to-use aqueous dilutions than in the aqueous dilutions based on the prior art.

Prior to application, formulations of fungal spores can be made up, for example, in a preliminary mixture with water in order to accelerate germination and reduce infection time (cf. H. D. Burges: *Formulation of Microbial Biopesticides, Springer,* 1998). Some manufacturers of microbial products (e.g. Remedier® from Isagro, Naturalist from CBC Europe, FZB24 from ABiTEP GmbH) likewise recommend activating the spores in the formulation prior to spray application. For this purpose, the formulation is diluted in a relatively small amount of water in a vessel (by a factor of 3-50) and left to stand for 2 to 24 hours prior to spraying. Since the microorganisms are particularly sensitive in this phase, it is advisable to use a carrier composition which is biocompatible in the formulation without any adverse effects on the microorganism. The active Ingredient composition according to the invention features a higher lifetime of microorganisms present at room temperature or slightly elevated temperatures. Thus, it is uncomplicated to store and to transport, and does not require any cooling in order to ensure that a sufficiently high concentration of germinable or viable microorganisms reaches the target locus on the plant or in the soil. In the ready-to-use aqueous dilutions, the carrier compositions or active ingredient compositions according to the invention do not impair the germination or growth of microorganisms at the target locus.

A further advantage is the biodegradability of the polyglycerol ester, of the carrier and of the composition comprising the carrier and the active microbiological ingredient. Biodegradability is preferably determined here by the OECD 301 F method. Further preferably, biodegradability is determined in accordance with OECD 301 F after 28 days at 22° C.

A further advantage is that the adhesion and retention of sprays/spray liquors containing the carrier composition or the active Ingredient composition on plant surfaces that are difficult to wet is also improved.

A further advantage is that the uptake of active ingredient by the cuticle and the vacuoles of the epidermal cells of the plant is activated. The effect of this is that the amount of crop protection compositions used can be reduced to cultivation, which has both environmental and economic advantages.

A further advantage is also very good rain resistance of the formulation on the plants after the water has evaporated. Even after rain, the active microbiological ingredient is present on the leaves. Thus, biological efficacy is assured even after rain.

A further advantage is the increase in yield. For instance, outdoor trials show that the carrier composition, either alone or in combination with the active microbiological Ingredient, has a yield-enhancing effect on agriculturally useful plants. A further advantage is therefore especially also the rise in effectiveness of biological pesticides. The Increase in yield from agriculturally useful plants and the enhancement of the effect of pesticides is successful for a multitude of crop plants. This can be observed in the case of both monocotyledonous and dicotyledonous plants. Since the action-enhancing effects are found in different crop plants, two different groups (the use of the term "group" should also be understood in the botanical sense) of the angiosperms, both monocotyledonous and dicotyledonous, it can be assumed that the effects will also be possible with other plants.

A further advantage is that the carrier and the active ingredient composition have anti-drift properties. Reduction in the drift capacity of the spray droplets is advantageous since a reduction in the contamination of the environment is thus brought about. Furthermore, the loss of costly active ingredients can be avoided, since these can be deployed in a higher percentage on the target area.

Within the scope of the invention, drift is understood as meaning the transversal locomotion of a spray from its place of origin. Drift is typically caused by environmental and/or ambient effects, for example wind. This wind can be of natural or artificial origin. Wind of artificial origin is, for example an air flow which is produced as a result of the locomotion of any vehicle on land or any aircraft in the air. The spray here is in all cases an aqueous medium. Preferably, the spray is formed by atomization in the air. Drift is preferably understood to mean the transverse locomotion of a spray from the site of origin by wind, the spray having formed as a result of atomization of an aqueous medium in the air. Anti-drift properties can preferably be quantified by the influence of the carrier composition or of the active ingredient composition on the droplet size distribution of the spray. There is a direct connection between the size of a droplet and its drift tendency—the finer the droplet, the greater the drift risk. The term “droplet size distribution” refers here to volume-weighted size distributions in a measurement of the diameters of the droplets in the spray mist. The droplet size distribution of a spray is dependent on the composition of the spray and also on the conditions during the spraying operation. Thus, for example, the type of construction of the spray nozzle used and also the selected spraying pressure have a significant influence on the resulting droplet size distribution. Preferably, the spray is generated using nozzles, preferably nozzles of the following designs: flat jet nozzles, wide-angle flat-jet nozzles, double flat-jet nozzles, hollow cone nozzles, filled cone nozzles, high-pressure nozzles, edge nozzles, as well as air injector nozzles, more preferably nozzles of the construction type of a flat-spray nozzle. Nozzles of this type are available, for example, from the manufacturers Lechler. TeeJet and/or Agrotop. Particular preference is given to flat-spray nozzles from TeeJet, with the nozzles of the type XR 11003 being very particularly preferred. Furthermore, preference is given to using a pressure of from 0.5 to 10 bar, preferably from 0.8 to 8 bar, more preferably from 0.9 to 6 bar, furthermore preferably from 0.95 to 2.5 bar and particularly preferably from 1 to 1.5 bar for generating spray. The effect of the carrier composition or of the active ingredient composition is always relative based on a spray of a formulation which does not feature the presence of the carrier composition or the active ingredient composition and is sprayed under identical conditions. A relative shift can be observed here in the volume-based maximum and/or in the volume-based median of the droplet size distribution of at least 5%, preferably at least 10%, especially at least 15%, based on the droplet size distribution of an Identical spray without carrier or without a composition composed of carrier and active microbiological Ingredient.

A further advantage is that the carrier facilitates the dispersion of the active microbiological ingredient in an aqueous composition, for example the spray liquor.

A further advantage is that the carrier can be made self-emulsifying. The carrier composition and the active ingredient composition can be readily dispersed in water. “Self-emulsifying” is understood to mean that the carrier or active ingredient composition can be dispersed in water without any great Input of shear and spontaneously forms emulsion droplets having an average size of less than 400 μm, preferably less than 200 μm, especially less than 100 μm. The size of the emulsion droplets can be determined, for example, by laser diffraction, for example by using laser diffraction systems or by computer-assisted image evaluation of high-resolution static images of the spray mist. The size of the emulsion droplets is preferably measured by laser diffraction, more preferably by using the MasterSizer 3000 from Malvern. Since efficiency enhancers for crop protection products are generally water-soluble in order thus to improve the efficacy of crop protection products from aqueous spray liquors, it is surprising in the light of the prior art that similar effects can also be achieved with self-emulsifying compositions. The self-emulsifying effect can especially be achieved by control of the hydrophobicity and/or water solubility of the polyglycerol ester preferably in combination with a suitable emulsifier. In the case of tankmix formulations, there is sufficiently homogeneous distribution of the polyglycerol ester in the spray liquor, for example even during the tankmixing operation. This facilitates firstly the preparation of spray liquors. Furthermore, it does not result in blockage of the spray nozzles as a result of the good incorporability and the associated homogeneous distribution during the spraying operation.

A further advantage is that polyglycerol esters can be prepared from natural raw materials. This is advantageous for the purposes of a sustainable economy.

A further advantage is that polyglycerol esters are of no concern with regard to health. In many cases, they have even been approved as a food additive, for example under number E475 (polyglycerol esters of edible fatty acids). All this is advantageous with regard to the residue problems described in the art.

The examples adduced hereinafter illustrate the present invention by way of example, without any intention of restricting the invention, the scope of application of which is apparent from the entirety of the description, to the embodiments specified in the examples.

EXAMPLES

Carrier Composition (Inventive)

The inventive carrier composition used was BREAK-THRU® SP 133 from Evonik, a mixture of 80% by weight of triglycerol trioleate and 20% by weight of polyethylene glycol-20 sorbitan trioleate.

Determining the Activity of Water of Compositions

To determine the activity of water of a sample, the air humidity is measured directly above a sample after attainment of equilibrium relative humidity (partial water vapour pressure differential). Equilibrium relative humidity (ERH) is measured in % relative humidity and is related to the $a_w$ value by the following relationship: $a_w$=ERH/100. The activity of water in the compositions was determined using the LabMaster-aW neo from Novasina.

Production of the Compositions with *Trichoderma harzianum*

Spores of the *Trichoderma harzianum* fungus were sourced from Rhizo-Mic UG and contained, according to elemental analysis, apart from the spores, about 75% by weight of $SiO_2$. The powder contained $1.97\times10^9$ germinable spores/g of product. The inventive active ingredient composition composed of BREAK-THRU® SP 133 and spores of *Trichoderma harzianum* was produced as follows: 3.60 g of the powder containing spores were weighed into a 50 ml centrifuge tube (e.g. sterile 50 ml tubes from Greiner Bio-One GmbH), and blanketed with 26.40 g of BREAK-THRU® SP 133. The mixture was mixed on a vortex shaker (lab dancer from Ika) for 30 seconds. After homogenization with a spatula, the composition, after a wait time of 15 minutes, was mixed again on a vortex shaker for 30 seconds. The composition produced contained $1.95\times10^8$ germinable spores/g. The compositions of the comparative examples were produced analogously. For the comparative examples, glycerol (ultrapure, min. 98%, anhydrous; Bernd Kraft GmbH), PEG 400 (Kollsolv® PEG E 400; Sigma Aldrich, average molar mass 320-420 g/mol), Pluronic® PE 6400

(BASF) and sunflower oil (food quality) were used as liquid carrier. The commercial WP formulation of *Trichoderma harzianum* was Trianum® P (Koppert).

Determination of Storage Stability

The compositions produced with spores of *Trichoderma harzianum* were incubated at 40° C. for four weeks, and the number of colony-forming units (CFU) was determined immediately after production (starting value) and after 7, 14, 21 and 28 days. The number of colony-forming units (CFU) is a measure of the number of spores that were able, before or after storage, to germinate and form colonies. To determine the number of colony-forming units (CFU), by the plating method, 1.0 g of the sample material was diluted with sterile physiological saline (0.9% by weight of NaCl in water) in a decimal dilution series down to the level of $10^{-8}$. The three dilution levels of $10^{-6}$, $10^{-7}$ and $10^{-8}$ (1.0 ml of each) were plated onto ready-made nutrient medium (Compact Dry YM for yeasts and mould fungi or Compact Dry Total Count from Nissui Pharmaceutical Co., Ltd.). The fungal spores were incubated at 25° C. for three days. Those plates on which 10-100 CFU are visible were evaluated. Table 1 shows the percentage of colony-forming units (in CFU/g) based on the starting value, as a measure of the survival rate or for the storage stability of the composition. The results shown are arithmetic averages from a triple determination.

TABLE 1

Storage stability experiments

| Composition | $a_w$ | Proportion of germinable spores after storage at 40° C.: 3) After 7 days | After 14 days | After 21 days | After 28 days |
|---|---|---|---|---|---|
| BREAK-THRU ® SP133 (88% by wt.) + *T. harzianum* spores (12% by wt.) 1) | 0.22 | 21% | 19% | 20% | 12% |
| *T. harzianum* spores 2) | 0.33 | 73% | 30% | 7% | 2% |
| Glycerol (80% by wt,) + *T. hazianum* spores (20% by wt.) 2) | 0.10 | 2% | 0.2% | n.d. 4) | n.d. 4) |
| PEG 400 (80% by wt.) + *T. harzianum* spores (20% by wt.) 2) | 0.05 | n.d. 4) | 21% | 9% | 2% |
| Pluronic ® PE 6400 (80% by wt) + *T. harzianum* spores (20% by wt) 2) | 0.20 | 26% | 18% | 8% | 1% |
| Sunflower oil (80% by wt.) + *T. harzianum* spores (20% by wt.) 2) | 0.40 | 50% | 15% | 10% | 0.4% |
| Commercially available WP formulation of *T. harzianum* 2) | 0.27 | 19% | 7% | 2% | 2% |

1) inventive example
2) comparative example
3) expressed as the percentage of colony-forming units (in CFU/g) based on the starting value
4) not determined The inventive example BREAK-THRU® SP 133 shows a distinct improvement in the survival rate after 28 days at 40° C. compared to the comparative examples including a commercially available *Trichoderma Harzianum* WP formulation.

Determination of Microbe Count in the Presence of Adjuvants

A determination of microbe count in the presence of 1% by weight of adjuvants was used to determine the effect thereof on the germinability or viability of different commercial microorganisms under application-relevant conditions. Comparative examples used were the Nu-Film®-P (Intrachem Bio Deutschland GmbH) and Wetcit (Oro Agri) adjuvants that have likewise been approved for biological cultivation. The commercial formulations were diluted with sterile physiological NaCl solution (0.9% by weight) with addition of 1.0% by weight of adjuvant in a decimal dilution series in a ratio of 1:100 000 to 1:1 000 000 000 and plated out on a suitable ready-made nutrient medium (Compact Dry from Nissui Pharmaceutical Co., Ltd.). Fungal spores and yeast cells were incubated at 25° C. for three days, bacterial spores at 30° C. for one day. Plates on which 10-100 CFU are visible were evaluated. Microbe count was determined as the arithmetic average from a triple determination. The microbe count was used to determine the percentage change in the number of colony-forming units by using the microbe count in the presence of BREAK-THRU® SP 133 as reference and setting it to 100%.

TABLE 2

Relative change in the number of colony-forming units of various commercial microorganisms with addition of adjuvants with BREAK-THRU ® SP 133 as reference

| Active ingredient | BREAK-THRU ® SP 133 1) | Nu-film ® 2) | WETCIT ® 2) |
|---|---|---|---|
| *Aureobasidium pullulans* (Botectol) | 100% | 44% | <0.01% |
| *Bacillus amyloliquefaciens* (FZB24) | 100% | 97% | <0.01% |
| *Coniothyrium minitans* (Contans) | 100% | 53% | <0.01% |
| *Trichoderma harziarium* (Trianum P) | 100% | 74% | <0.02% |

1) inventive example
2) comparative example

The results show that BREAK-THRU® SP 133 is very mild compared to other adjuvants and the growth of various microorganisms is not impaired.

Determination of Retention

In order to verify whether the Inventive carrier composition BREAK-THRU® SP 133 is able to improve the retention of spray liquors on the crop plant, a study was conducted at the Plant Protection Chemistry Institute in New Zealand (PPCNZ). The model plant used was spinach (*Spinacia oleracea* var. Perpetual). Based on contact angle measurements on the adaxial leaves of the plant, spinach is rated as "moderately difficult to wet". For comparison, a polyether-modified trisiloxane (BREAK-THRU® S 240, Evonik) was employed as a conventional adjuvant known from the prior art. The spinach plants were bought as 4-week-old seedlings from a garden centre and sown in individual pots. These were then cultivated further in a growing chamber under controlled environmental conditions (20° C. by day, 15° C. by night, 75% rh, with a photoperiod lasting for 12 h). At the time of the experiment, the plants were then 6 weeks old and 7 cm high.

Retention was determined using a moving head track sprayer that sprayed the spray liquors made up onto the trial plants. The dye tartrazine was added to the spray liquors used in an amount of 8 g/l. Each variant included 25 repetitions/plant and was treated at 100 l/ha by means of a flat-jet air Induction nozzle (AI 95015EVS) at pressure 250 kPa and a flow rate of 0.58 l/min. The nozzles were secured 50 cm above the height of the plants (7 cm). In order to verify the application rate, artificial collectors (plastic dishes repeated four times per variant) were secured horizontally at the level of the average plant height.

After deployment of the spray liquor, three leaves were collected by sampling from each repetition and washed Immediately with deionized water. The artificial collectors were also washed with deionized water immediately after application.

The tartrazine dye added to the spray liquor was then quantified by spectrophotometry at 427 nm. The leaf area was determined by means of a leaf area measuring device (Licor LI 3100A). Then the amount of spray remaining was calculated (table 3). The results were calculated by means of variance analysis and LSD test (P=0.05) using the Statistix computer program. If necessary, the data were transformed prior to the analysis.

TABLE 3

| Retention trials | | | |
|---|---|---|---|
| Additive | Concentration % w/v | Retention in μl/cm$^2$ | Retention in % |
| BREAK-THRU ® SP 133[1)] | 0.1 | 0.68 a | 68.2 a |
| BREAK-THRU ® S 240[2)] | 0.1 | 0.56 b | 55.6 b |

[1)] inventive example

[2)] comparative example

The results given in Table 3 show that the retention of the spray liquor with the inventive carrier BREAK-THRU® SP 133 is significantly Improved compared to the comparative example BREAK-THRU® S 240 on spinach leaves.

The invention claimed is:

1. A composition, comprising:

at least one active microbiological ingredient, and a carrier, comprising at least one polyglycerol ester, for the at least one active microbiological ingredient;

wherein a proportion by mass of the carrier based on a total mass of the composition is 40% to 99%;

wherein a proportion by mass of the at least one polyglycerol ester based on the total mass of the carrier is 60% to 100%, and wherein the at least one active microbiological ingredient is selected from the group consisting of *Bacillus Subtilis, Trichoderma harzianum, Bacillus amyloliquefaciens, Beauveria bassiana, Metarhizium rileyi, Metarhizium anisopliae, Clonostachys rosea, Aureobasidium pullulans, Coniothyrium minitans*, and their organs, and wherein the carrier optionally comprises at least one emulsifier, wherein the at least one emulsifier is selected from the group consisting of a sorbitan fatty acid ester and an ethoxylated sorbitan fatty acid ester, and wherein the at least one polyglycerol ester comprises triglycerol trioleate.

2. The composition according to claim 1, wherein the at least one polyglycerol ester has an HLB value of not more than 8.

3. The composition according to claim 1, wherein the carrier comprises the at least one emulsifier, and wherein the at least one emulsifier has an HLB value of not less than 9.

4. The composition according to claim 1, wherein the carrier comprises the at least one emulsifier.

5. The composition according to claim 4, wherein acyloxy radicals of the sorbitan fatty acid ester or the ethoxylated sorbitan fatty acid ester have 4 to 40 carbon atoms, and/or wherein the sorbitan fatty acid ester or the ethoxylated sorbitan fatty acid ester has 0 to 40 oxyethylene groups.

6. The composition according to claim 4, wherein the at least one active microbiological ingredient is selected from the group consisting of *Trichoderma harzianum*, and *Beauveria bassiana*.

7. The composition according to claim 1, wherein the at least one polyglycerol ester is triglycerol trioleate, wherein the carrier comprises the at least one emulsifier, and the at least one emulsifier is polyethylene glycol-20 sorbitan trioleate.

8. The composition according to claim 1, further comprising a proportion by mass of emulsifier based on the total mass of the carrier of more than 0% to 40%.

9. The composition according to claim 8, wherein the carrier comprises the at least one emulsifier, and wherein the proportion by mass of the at least one polyglycerol ester based on the total mass of the carrier is 75% to 85%, and the proportion by mass of the at least one emulsifier based on the total mass of the carrier is 15% to 25%.

10. The composition according to claim 1, wherein the at least one active microbiological ingredient comprises spores.

11. The composition according to claim 1, wherein the at least one active microbiological ingredient comprises spores of *Trichoderma harzianum*.

12. The composition according to claim 1, wherein the $a_w$ value of the carrier is less than 0.4.

13. The composition according to claim 1, wherein the composition is a composition for treatment of plants, seed, or soil; or a biostimulant.

14. The composition according to claim 1, wherein the carrier comprises at least one additional emulsifier, in addition to the at least one emulsifier selected from the group consisting of a sorbitan fatty acid ester and an ethoxylated sorbitan fatty acid ester.

15. The composition according to claim 1, wherein the organs are selected from the group consisting of spores, conidia, blastospores, chlamydospores, sclerotia, and hypha segments.

16. The composition according to claim 1, wherein the carrier provides increased storage stability of the at least one active microbiological ingredient compared to a carrier without the at least one polyglycerol ester.

17. The composition according to claim 1, wherein the at least one active microbiological ingredient is selected from the group consisting of *Trichoderma harzianum, Bacillus Subtilis*, and *Beauveria bassiana*.

18. A method of increasing the storage stability of the at least one active microbiological ingredient in the composition according to claim 1, the method comprising:

storing the at least one active microbiological ingredient in the composition.

* * * * *